US012584085B2

(12) United States Patent
Catarino Ribeiro et al.

(10) Patent No.: US 12,584,085 B2
(45) Date of Patent: Mar. 24, 2026

(54) MICROFLUIDIC DEVICE FOR A 3D TISSUE STRUCTURE

(71) Applicant: River BioMedics B.V., Enschede (NL)

(72) Inventors: Marcelo Catarino Ribeiro, Amersfoot (NL); Tom Mathijs Paulus Maria Boonen, Enschede (NL)

(73) Assignee: River BioMedics B.V., Enschede (NL)

( * ) Notice: Subject to any disclaimer, the term of this patent is extended or adjusted under 35 U.S.C. 154(b) by 780 days.

(21) Appl. No.: 17/917,816

(22) PCT Filed: Apr. 8, 2021

(86) PCT No.: PCT/NL2021/050227
§ 371 (c)(1),
(2) Date: Oct. 7, 2022

(87) PCT Pub. No.: WO2021/206551
PCT Pub. Date: Oct. 14, 2021

(65) Prior Publication Data
US 2023/0137145 A1 May 4, 2023

(30) Foreign Application Priority Data
Apr. 9, 2020 (EP) ..................................... 20169095

(51) Int. Cl.
C12M 3/00 (2006.01)
C12M 1/00 (2006.01)
(Continued)

(52) U.S. Cl.
CPC ............ C12M 21/08 (2013.01); C12M 23/16 (2013.01); C12M 23/26 (2013.01); C12M 23/40 (2013.01);
(Continued)

(58) Field of Classification Search
None
See application file for complete search history.

(56) References Cited

U.S. PATENT DOCUMENTS

2007/0275455 A1 11/2007 Hung et al.
2014/0057311 A1 2/2014 Kamm et al.
(Continued)

FOREIGN PATENT DOCUMENTS

EP 3190172 A2 7/2017
WO 2015/013210 A1 1/2015
WO 2016/174607 A1 11/2016

OTHER PUBLICATIONS

International Search Report dated Jul. 2, 2021, issued in corresponding International Application No. PCT/NL2021/050227 (3 pgs.).
(Continued)

*Primary Examiner* — Holly Kipouros
(74) *Attorney, Agent, or Firm* — Pillsbury Winthrop Shaw Pittman, LLP

(57) ABSTRACT

Microfluidic device comprising at least one cell culture unit for forming, culturing, growing and/or maintaining a 3D tissue structure such as a 3D strip of cardiac tissue, wherein the at least one cell culture unit comprises: a respective culture chamber for culturing cells having a chamber outlet opening; and a cell supply channel arranged to guide a microfluidic flow of liquid holding cells between a channel inlet and a channel outlet, wherein the cell supply channel is provided with a flow inhibitor which is operable to selectively provide a flow inhibiting state or a flow permitting state depending on a fluid pressure at the flow inhibitor, wherein, in the flow inhibiting state, the flow inhibitor is configured to substantially inhibit liquid flow between the cell supply channel and the culture chamber, wherein, in the flow permitting state, the flow inhibitor is configured to permit such liquid flow such that the cell supply channel is (Continued)

in liquid communication with the culture chamber to supply the culture chamber with cells, wherein the culture chamber is provided with at least two mutually spaced apart elastic support structures which extend in the culture chamber and which are configured for elastically supporting a tissue formed in the culture chamber, in particular a cultured 3D tissue formed from the cells, wherein the elastic support structures are elastically deformable, in particular flexible, in particular to vary a mutual distance of said support structures under influence of a varying contraction force between said support structures.

29 Claims, 7 Drawing Sheets

(51) Int. Cl.
|  |  |
|---|---|
| *C12M 1/12* | (2006.01) |
| *C12M 1/34* | (2006.01) |
| *C12M 3/06* | (2006.01) |
| *C12N 5/077* | (2010.01) |

(52) U.S. Cl.
CPC ............ *C12M 25/04* (2013.01); *C12M 41/46* (2013.01); *C12N 5/0657* (2013.01); *C12N 2506/45* (2013.01); *C12N 2513/00* (2013.01); *C12N 2533/56* (2013.01)

(56) References Cited

U.S. PATENT DOCUMENTS

| | | | |
|---|---|---|---|
| 2017/0130187 A1* | 5/2017 | Lee | B01L 3/502738 |
| 2019/0276785 A1* | 9/2019 | Vunjak-Novakovic | C12M 1/34 |

OTHER PUBLICATIONS

Written Opinion of the International Searching Authority dated Jul. 2, 2021, issued in corresponding International Application No. PCT/NL2021/050227 (7 pgs.).

Hansang Cho et al., "How the Capillary Burst Microvalve Works", Journal of Colloid and Interface Science, Academic Press, Inc. US, Nov. 2006, v. 306, No. 2, pp. 379-385.

T.M.P.M. Boonen, "Development of a Myocardial Infarction Model by the Design of a Miniaturized 3D Culture Platform", University of Twente, Faculty of Science and Technology Department of Applied Stem Cell Technologies, Oct. 18, 2019, 42 pgs.

* cited by examiner

MICROFLUIDIC DEVICE FOR A 3D TISSUE STRUCTURE

CROSS-REFERENCE TO RELATED APPLICATIONS

This application is the U.S. National Stage of PCT/NL2021/050227, filed Apr. 8, 2021, which claims priority to European Patent Application No. 20169095.5, filed Apr. 9, 2020, the contents of each of which are incorporated herein by reference in their entireties.

FIELD

The invention relates to a microfluidic device comprising a cell culture unit for forming, culturing, growing and/or maintaining a 3D tissue structure. The invention further relates to a method of forming, culturing, growing and/or maintaining a 3D tissue structure, to a method of performing an assay on such a structure, to a system for performing such an assay, and to use of such a microfluidic device.

BACKGROUND

The process of drug discovery and development is often hampered by a low specificity and efficacy of newly developed drugs in combination with unexpected detrimental side effects, leading to a high attrition rate. Consequently, the process of drug discovery and development is usually a very costly and long process. Despite increased worldwide expenditure for development the actual number of new molecular entities reaching the market is declining. For example cardiovascular diseases, including channelopathies, cardiomyopathies, and myocardial infarction, are the major cause of morbidity and mortality worldwide, and still there is no fully effective treatment available. New drugs for these diseases are not reaching patients because the development of cardiovascular drugs through clinical trials has a failure rate of 91.8%. The reason for this excessive failure rate is the lack of proper target and drug validation during the pre-clinical study phases. Currently, pre-clinical studies rely on animal models, which are known to have an insufficient predictive value of the human heart, and 2D cell culture models, which do not reliably mimic the complex human heart function and consequently provide insufficient insights in human disease mechanisms. These limitations severely compromise the predictability and validity of these models, which in turn significantly decrease the chances of drug success during human clinical trials.

The use of human stem cells and in particular the groundbreaking discovery of the generation of human induced pluripotent stem cells (hiPSC) opened the door to personalized medicine, i.e. using patient-derived cells for human in vitro disease modelling and production of human specialized cell types for regenerative medicine. In the past years a new 3D model has been developed based on assembling human induced pluripotent stem cells (hiPSC)-derived cardiomyocytes into a three-dimensional strip configuration (3D cardiac strip). This 3D strip has been established by the scientific community as a consistent human model with a human predictivity level of 80%, thereby becoming the gold standard in the field. However, this first-generation gold-standard is labor intensive to fabricate and requires around 500,000 to 1,000,000 cells to form one single strip, resulting in a significant commercial cost price per strip, while generating only one data point per strip. Since each compound should to be tested in six different concentrations, with each concentration requiring three technical repeats, testing each drug would provide high costs per drug tested. Current methods for target finding and drug discovery depend on screening thousands to millions of compounds per run in order to find a lead compound. Running a drug discovery screen with 10 to 100 thousand compounds using this technology in its current form is in view of total costs not feasible for a high-throughput screening during pre-clinical drug discovery.

There is thus a need to miniaturize the above described 3D human cardiac strips and associated tests, preferably to microscale. The known method to make 3D cell tissues is based on casting cells, e.g. hPSC-cardiomyocytes, surrounded by extracellular matrix (ECM) such as Matrigel, collagen I and fibrin, in an open-top mold for culturing the cell tissue therein. A drawback of using molds for preparing a microscale 3D-strip is that in order to decrease the size of the strips one must make micrometer sized molds and be able to accurately pipette into the mold chamber. Due to the volume of the mold chamber required being very small, such a process would be impractical and unreliable. One further major challenge in this respect is that the volume of cell-containing fluid to be pipetted has to be very small. The optimal cell seeding density to make 3D cardiac strips is between 10 million cells/mL and 20 million cells/mL, and the acceptable number of hiPSC-cardiomyocytes per strip is approximately 1,000 cells. This means that 100 nanoliter need to be pipetted into a mold that is micrometer sized. Pipetting these small volumes containing live cells into such small molds in a consistent manner is extremely difficult.

A solution is to use a microfluidic device comprising a cell culture unit for culturing small tissue structures from cells. Such a microfluidic device is known to comprise one or more microfluidic channels which can supply cells and matrix to a culture chamber for culturing small cell tissue structures. A drawback of the known microfluidic device is that the cell and matrix would become evenly distributed through the culture chamber and microfluidic channels resulting in 3D tissue to be formed both inside and outside the chamber as an interconnected tissue, which may interfere with the mechanical behavior of the tissue and with potential interesting measurements of the tissue, such as measurements of contraction force of 3D cardiac strips.

Thus, there is a need for an improved microfluidic device and an improved method of culturing a 3D tissue structure.

SUMMARY

An object of the present disclosure is to enable improved culturing of a 3D tissue structure, in particular many of such 3D tissue structures, in a microfluidic device, wherein in particular the location or locations of culturing can be better controlled, the culturing being in particular substantially confined or confinable to designated culture chambers. An object is to provide a microfluidic device wherein one or more culture chambers can be efficiently and reliably provided with cells for culturing a 3D tissue. An object is to provide a method and platform for reliably and efficiently performing biological assays, in particular 3D tissue assays with a relatively high throughput. An object is to provide a device wherein a relatively large number of assays, e.g. 3D tissue assays, can be performed in parallel, in particular without cross contamination, in particular relatively efficiently and/or with a high throughput. An object is to enable miniaturization of cardiac tissue cultures such as microscale 3D cardiac strips, in particular for increasing the number of assay units per culturing area, in particular for more efficient drug discovery. An object is to at least partially solve at least one of the problems mentioned in the background section, or a related problem.

To that end, an aspect of the present disclosure provides a microfluidic device comprising at least one cell culture unit for forming, culturing, growing and/or maintaining a 3D tissue structure such as a 3D strip of cardiac tissue. The at least one cell culture unit comprises a respective culture chamber for culturing cells having a chamber outlet opening; and a cell supply channel arranged to guide a microfluidic flow of liquid holding cells between a channel inlet and a channel outlet.

The cell supply channel is provided with a flow inhibitor which is operable to selectively provide a flow inhibiting state or a flow permitting state depending on a fluid pressure at the flow inhibitor.

In the flow inhibiting state, the flow inhibitor is configured to substantially inhibit liquid flow between the cell supply channel and the culture chamber. In the flow permitting state, the flow inhibitor is configured to permit such liquid flow such that the cell supply channel is in liquid communication with the culture chamber to supply the culture chamber with cells.

The flow inhibitor is preferably arranged adjacent the respective culture chamber, in particular at a connection between the cell supply channel and the culture chamber. Accordingly, a maximum distance between the culture chamber and the flow inhibitor may be in the range of 0 to 100 μm, preferably in the range of 0 to 50 μm, more preferably in the range of 0 to 10 μm.

In this way, cells are substantially prevented from residing in a section of the device between the culture chamber and the flow inhibitor. Without wishing to be bound by theory, it is believed that this effect results from several factors, including the limited initial opportunity for cells to reside in said section due to the limited volume thereof, as well as the tendency of cells close to the culture chamber to move into the culture chamber as part of the process of tissue formation.

Such a microfluidic device thus enables easy supply of cells into the culture chamber when the flow inhibitor is in the flow permitting state. In the flow inhibiting state, the flow inhibitor can prevent cells from exiting the culture chamber. Also in the flow inhibiting state, the flow inhibitor can inhibit fluids such as a rinsing liquid from entering the culture chamber so that e.g. the cell supply channel can be rinsed after supplying the cells to the culture chamber. In this way, cell culturing outside the designated culture chamber can be effectively and efficiently prevented. This is of particular relevance for correct microscale formation of contracting 3D cell tissues such as muscular cell tissues, specifically cardiac tissue such as 3D cardiac strips, as any deviation from the desired shape of the tissue as a result of cell growth outside the culture chamber may influence the tissue properties, in particular with respect to contraction of the tissue.

In the context of the present disclosure, a flow inhibitor can thus be understood as selectively operable in one of two distinct states, i.e. a flow inhibiting state and a flow permitting state, in a way that is functionally similar to a valve being operated either in a closed state or in an open state, respectively. Since said states of the flow inhibitor are distinct, a mere flow resistance does not by itself constitute a flow inhibitor as in the present context. As will be elaborated later on, examples of a flow inhibitor according to the present disclosure include a capillary burst valve and a quake valve, among other microfluidic valve structures.

In the context of the present disclosure, a 3D (i.e. three-dimensional) tissue structure can be understood as a tissue structure comprising multiple live cells which are positioned with respect to each other in more than one plane. Thus, for example, when three cells of the tissue structure together define a plane, one or more further cells of the same tissue structure are positioned at a distance from said plane. Such a 3D tissue structure can for example form a strip like structure have a strip thickness corresponding to more than one cell, i.e. two cells or more. For example the microfluidic device may be configured for forming, culturing, growing and/or maintaining a 3D tissue structure such as a 3D strip of cardiac tissue in the at least one cell culture unit by providing the culture chamber with a length and width such that a tissue structure in a first plane is allowed to grow and a height which allows more than one cell, i.e. two cells or more, to grow in the height direction on top of each other to form the 3D tissue structure while the supply channel or channels are configured and arranged to supply media to the culture chamber such that a majority or at least substantially all cells in the 3D tissue structure remain alive. The culture chamber is provided with at least two mutually spaced apart elastic support structures, for example mainly made from silicon and/or plastic, which extend in the culture chamber and which are configured for elastically supporting a tissue formed in the culture chamber, in particular a cultured tissue formed from the cells. The elastic support structures are preferably elastically deformable, in particular flexible, in particular to vary a mutual distance of said support structures under influence of a varying contraction force between said support structures.

Such a configuration enables the formation and culturing of a 3D tissue structure, for example a strip-like structure, of tissue which mechanically interacts with the support structures. This can be particularly advantageous in the case of muscle tissue, in particular heart muscle tissue, wherein the formed tissue structure is allowed to e.g. periodically contract and relax against an elastic load provided by the support structures.

Optionally at least one, preferably each, of the elastic support structures comprises a respective elastic beam, in particular a flexible beam, which is connected to and extends from a wall, in particular a top wall, of the culture chamber. Preferably a main longitudinal beam axis of the elastic beam, in particular in an unloaded state, extends at an angle to said wall, preferably an angle between 45 and 135 degrees, for example an angle of about 90 degrees. Preferably said wall extends substantially in parallel to a main device plane in which the microfluidic device extends.

It has been found that such a configuration can provide good structural and functional support for a cultured tissue structure in the culture chamber, in particular for a strip-like tissue structure which extends and contracts substantially in the main device plane. A thus formed tissue structure can be studied easily and efficiently, for example in terms of contraction properties of the tissue structure, wherein in particular a large number of such tissue structures can be efficiently studied in parallel, yielding a high assay throughput.

Optionally at least one, preferably each, of the elastic support structures extents from the top wall of the culture chamber in the direction of an opposite bottom wall of the culture chamber with a free outer end of the elastic support structure, e.g a tip of the elastic support structure, being positioned near but at a distance of the bottom wall. Optionally at least one, preferably each, of the elastic support structures narrows from a stable base portion of the elastic support structure connected to the top wall to the free outer end, e.g. flexible tip, of the elastic support structure.

Optionally at least one, preferably at least two, of the elastic support structures comprises an electrode configured for determining an electrophysiological property of the 3D tissue structure.

The tissue structure can thus be easily and efficiently studied in terms of electrophysiological properties, in particular with a high throughput. Relevant examples of such an electrophysiological property include: membrane depolarization velocity, resting membrane potential, action potential amplitude, action potential duration and Q-T interval.

Preferably, the device, in particular one or more of the elastic support structures, is configured to enable, during use, determination of one or more contraction properties of an associated 3D tissue structure. Examples of such contraction properties include: contraction force, contraction time, contraction speed, relaxation time, relaxation speed, contraction duration and contraction interval. To that end, the elastic support structures are preferably designed such that one or more of their mechanical properties, in particular elasticity properties such as Young's modulus, are thereby known, in particular with a relatively high precision to enable relatively precise determination of the one or more contraction properties. Such determination is preferably carried out using a video camera for recording contraction and/or relaxation movements of the 3D tissue structure. Alternatively or additionally, to enable such determination, the device, in particular the elastic support structures, can be provided with one or more of: a piezo-electric sensing element; means for sensing an electrical resistance; and a light sensor.

The elastic support structures can be mutually spaced apart by a distance of between 0.1 and 10 mm, preferably between 0.1 and 5 mm, preferably between 0.1 and 3 mm, preferably between 0.1 and 2 mm, preferably between 0.1 and 1 mm, for example about 0.6 mm or about 0.9 mm.

Such a distance may be designed as a function of another dimension or dimensions of the culture chamber. Good dimensioning and/or shaping of the cultured tissue structure can be realized in this way. Particularly such a distance between the elastic support structures allows formation of a microscale 3D cell tissue structure with a suitable length for testing and experimentation of the contraction properties of the tissue with a minimum amount of cells in the tissue, e.g. a 3D cardiac strip tissue of approximately 1000-2000 cells.

Preferably a bottom wall of the culture chamber is configured to allow imaging of the interior of the culture chamber through said bottom wall using confocal microscopy, in particular in the visible spectrum. To that end at least part of the bottom wall can be substantially transparent. Optionally the top wall of the culture is at least substantially transparent as well. Preferably a thickness of the bottom wall is in the range of 1 to 1000 µm, preferably in the range of 100 to 500 µm, for example about 150 µm.

Such imaging, for example video imaging, can advantageously enable visual studying, e.g. testing, of the tissue structure in the culture chamber.

The at least one cell culture unit may comprise an outlet channel in fluid communication with the culture chamber separate from the supply channel. During use preferably at least one of the outlet channel and the supply channel provides a vent for the culture chamber.

In this way the culture chamber is vented in use upon supply of liquid through the supply channel, e.g. for pressure relief and/or dissipation of a gas in the chamber.

The device may comprise the at least one cell culture unit in an array of cell culture units, in particular a two-dimensional array. Preferably the array comprises a number of cell culture units in the range of 10 to 2000, more preferably in the range of 50 to 1536, more preferably in the range of 100 to 500, for example about 200 or about 384.

Many tissue assays can thus be performed easily and efficiently in parallel, yielding a high throughput.

In one class of embodiments, the flow inhibitor can be formed by a flow path section of the cell supply channel arranged as a capillary burst valve which is operable by change of a liquid flow pressure of the liquid flowing in the flow path section of the channel. The flow inhibitor can thus be configured to be operated in the flow permitting state by providing liquid with a liquid flow pressure exceeding a threshold flow pressure value, wherein the flow inhibitor is configured to be operated in the flow inhibiting state by providing liquid with a liquid flow pressure below the threshold flow pressure value.

Capillary burst valves are known as such in the context of microfluidic devices. Such a capillary burst valve can thus advantageously provide the flow inhibitor in a microfluidic device according to the present disclosure.

The capillary burst valve may provide a substantially bidirectional capillary burst valve. To that end preferably the flow path section is shaped with a central flow constriction, the flow path section being substantially symmetrical with respect to a plane of symmetry which is transverse to the flow path section at the central flow constriction.

Such a bidirectional burst valve can thus enable flow inhibition by the flow inhibitor in two opposite directions depending on respective pressures at the burst valve. Alternatively the burst valve can be substantially unidirectional, thus for example (more) inhibiting cells exiting the culture chamber while (more) enabling cells entering the culture chamber.

Measured in a transverse plane to the flow path, the flow constriction preferably has a smallest diameter in the range of 0.01 to 1 mm preferably in the range of 0.01 to 0.5 mm, for example about 0.1 mm.

Good results have been obtained in this way, wherein in particular a good capillary burst valve behavior can thus be provided.

Alternatively or additionally, for example in another class of embodiments, the flow inhibitor may comprise a quake valve comprising a valve control chamber and a flexible membrane which liquid-tightly separates the cell supply channel from the valve control chamber, the valve control chamber being fluidly connected to a valve control channel for supplying control fluid to the control chamber to provide a fluid pressure in the valve control chamber.

The flow inhibitor may thus be changeable from the flow inhibiting state to the flow permitting state by reducing the fluid pressure in the valve control chamber with respect to a fluid pressure in the cell supply channel, wherein the flow inhibitor is changeable from the flow permitting state to the flow inhibiting state by increasing the fluid pressure in the valve control chamber with respect to the fluid pressure in the cell supply channel.

In the flow inhibiting state the flexible membrane can be shaped to liquid-tightly seal the supply channel to inhibit liquid flow between the cell supply channel and the culture chamber, wherein in the flow permitting state the flexible membrane is shaped to allow liquid flow between the cell supply channel and the culture chamber.

Quake valves are known as such in the context of micro-fluidic devices. Such a quake valve can thus advantageously provide the flow inhibitor in a microfluidic device according to the present disclosure.

The respective cell supply channels of the cell culture units can be fluidly connected to each other upstream of the flow inhibitor, in particular connected to a common cell supply inlet of the microfluidic device.

Since the quake valves enable control of the flow inhibitor substantially independent of a fluid pressure in the cell supply channel, improved cell supply efficiency and reli-ability can thus be provided, wherein for example a flow of liquid holding cells is directed from the common cell supply inlet first into a respective culture chamber of one cell culture unit and subsequently into a respective culture chamber of another cell culture unit by controlling the respective quake valves of said cell culture units accord-ingly.

Optionally, respective valve control chambers of at least two different cell culture units are fluidly connected to the same valve control channel for contemporaneously chang-ing a fluid pressure in each of the respective valve control chambers.

Cell supply to the respective culture chambers of the at least two units can thus be controlled efficiently using a same valve control channel.

Optionally, each cell culture unit comprises a respective agent supply channel arranged to guide a microfluidic flow of liquid holding an agent between an agent inlet and an agent outlet, wherein for each cell culture unit the device is configured to permit a flow of liquid from the respective agent supply channel to the respective culture chamber of the cell culture unit while at the same time inhibiting a flow of liquid from said agent supply channel to one or more, preferably all, culture chambers of the other cell culture units of the device.

An agent can be a pharmaceutical compound, for example a drug to be tested, among other options. In this way, respective culture chambers of different cell supply units can be separately provided with one or more agents, in particular without cross contamination among the cell culture units.

The agent supply channel may fluidly connect to a path section of the cell supply channel which section is upstream of the flow inhibitor, wherein the cell supply channel is provided with a further flow inhibitor, in particular a quake valve, which is arranged upstream of said section of the cell supply channel and configured to inhibit, at least selectively inhibit, a flow of liquid from said section to a cell supply channel of another one of the cell culture units.

A number of fluid connections to the culture chamber can thus be reduced, providing a reliable and compact configu-ration. Meanwhile cross contamination of agents among different cell culture units can thus be effectively prevented.

Preferably the agent supply channel is provided with a respective flow inhibitor, in particular a quake valve, for selectively inhibiting a liquid flow through the agent supply channel.

In this way a flow of liquid holding an agent through the agent supply channel can be better controlled. Also, cells can thus be prevented from traveling through the agent supply channel e.g. into the agent inlet.

The cell supply channel may be provided with a bypass channel arranged to guide a flow of liquid between the channel inlet and the channel outlet and/or a flow of liquid between the agent inlet and the agent outlet without entering the respective culture chamber. Preferably the bypass chan-nel is provided with one or more respective flow inhibitors, in particular one or more quake valves, for selectively inhibiting a liquid flow through the bypass channel.

Such a bypass channel can provide pressure relief e.g. when the respective culture chamber is substantially closed off by the respective flow inhibitor. Respective flow inhibi-tors of the bypass channel can help to selectively direct a flow of liquid holding cells into the respective culture chamber.

A further aspect of the present disclosure provides a method of forming, culturing, growing and/or maintaining at least one 3D tissue structure such as a strip of cardiac tissue. The method comprises: providing a microfluidic device as described above; supplying cells for the tissue structure into the respective culture chamber of the at least one cell culture unit via the cell supply channel, wherein the respective flow inhibitor is operated in the flow permitting state; and sub-sequently operating the respective flow inhibitor in the flow inhibiting state, thereby inhibiting the cells from exiting the culture chamber via the flow inhibitor. Subsequently oper-ating the flow inhibitor in the flow inhibiting state may comprise controlling a fluid pressure at the flow inhibitor, for example a fluid pressure in a respective valve control chamber.

Such a method can provide above-mentioned advantages.

When the microfluidic device comprises the at least one cell culture unit in an array of cell culture units and the respective cell supply channels of the cell culture units are fluidly connected to a common cell supply inlet, supplying cells into the respective culture chamber of the at least one cell culture unit preferably comprises supplying cells for a plurality of cell culture units into the common cell supply inlet and subsequently allowing the cells to travel from said cell supply inlet through the respective cell supply channels to the respective culture chambers, for example subse-quently to neighboring culture chambers.

Cells for forming 3D tissue structures in the respective culture chambers can thus be efficiently and reliably sup-plied, in particular to a large number of culture chambers.

The method may further comprise supplying an agent, for example a pharmaceutical compound, into the culture cham-ber, for example subsequently via a respective agent inlet and a respective agent supply channel of the respective cell culture unit.

Different culture chambers may thus be supplied with different agents, e.g. different concentrations and/or different doses of a pharmaceutical compound and/or different com-pounds, enabling relevant comparisons in an assay. High throughput screening assays on 3D tissue structures can thus be enabled.

The method may further comprise: supplying a gellable substance into the respective culture chamber, preferably together with supplying the cells, wherein for example the gellable substance and the cells are together supplied in a microfluidic flow of liquid through the cell supply channel; and subsequently allowing the gellable substance to form a gel in the culture chamber, thereby suspending cells in the culture chamber in the formed gel.

It has been found that in this way a 3D tissue structure can be formed in the culture chamber, in particular efficiently and reliably.

The gellable substance preferably forms a biodegradable gel in the culture chamber, wherein the method preferably comprises allowing the cells in the culture chamber to at least partly degrade the biodegradable gel, preferably such that the cells migrate towards each other during the at least partial degrading to form a clump of cells in the culture chamber, in particular a clump of cells together forming a 3D tissue structure which connects to one or more, e.g. the, elastic support structures in the culture chamber.

In this way the formed tissue structure can be formed, in particular such that the structure has space to move, e.g. contract and relax, within the culture chamber.

A further aspect provides a method of performing an assay on at least one 3D tissue structure, comprising: forming at least one 3D tissue structure as described above, for example a strip of cardiac tissue, in particular using a microfluidic device as described above; and measuring an activity of the at least one 3D tissue structure, in particular a tissue movement and/or an electrical activity.

Assays on 3D tissue structures can thus be performed more efficiently and/or more reliably, wherein in particular a relatively low number of cells can yield a relatively large number of assay data points.

A further aspect provides a system for performing an assay on at least one 3D tissue structure. The system comprises: a microfluidic device as described above; and a measurement device, for example comprising a video camera, for measuring a property and/or an activity of the at least one 3D tissue structure.

An assay as described above, in particular a high through-put assay, can advantageously be performed with such a system.

The system may further comprise a source of cells for supplying cells to the at least one culture chamber via an inlet of the device. The source of cells can comprise a pipetting device containing cells, for example.

The system may further comprise a pump for changing a fluid pressure in the device, for example in the cell supply channel and/or at one or more flow inhibitors.

A further aspect provides use of a microfluidic device as described above for forming, culturing, growing and/or maintaining, and studying, at least one 3D tissue structure, preferably an array of separate 3D tissue structures in respective culture chambers, wherein preferably the number of separate 3D tissue structures in the array is in the range of 10 to 1000, more preferably in the range of 50 to 1536, more preferably in the range of 100 to 500, for example about 200 or about 384.

Such use provides above-mentioned advantages.

BRIEF DESCRIPTION OF THE DRAWINGS

In the following detailed description, the invention will be explained further using exemplary embodiments and drawings. The drawings are schematic and merely show examples. Similar or corresponding elements have been provided with similar or corresponding reference signs. In the drawings:

FIG. 1b shows an isometric view of the cell culture unit of FIG. 1a;

FIG. 2b shows an isometric cross section view of the device of FIG. 2a along the line II-II in FIG. 2a;

FIG. 5b shows a partial isometric view of the device of FIG. 5a;

FIG. 7b shows a cross section view of the tissue structure of FIG. 7a along the line VII-VII in FIG. 7a.

DETAILED DESCRIPTION

Figure 2A:
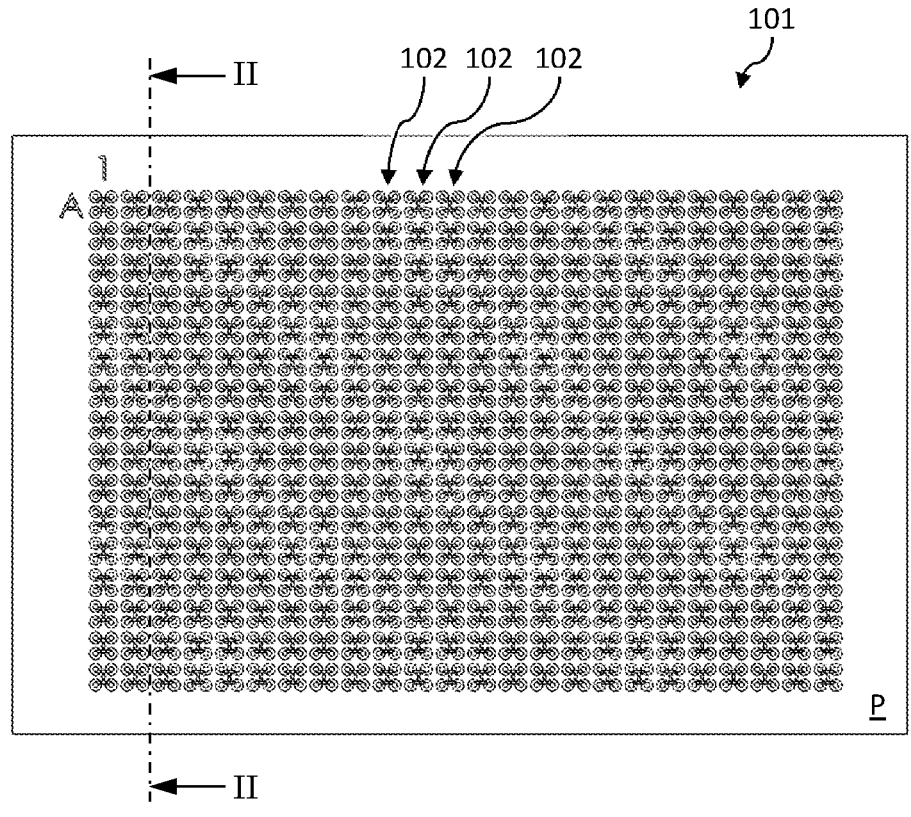
FIG. 2a shows a top view of the microfluidic device of FIGS. 1a and 1b.
Figure 2B:
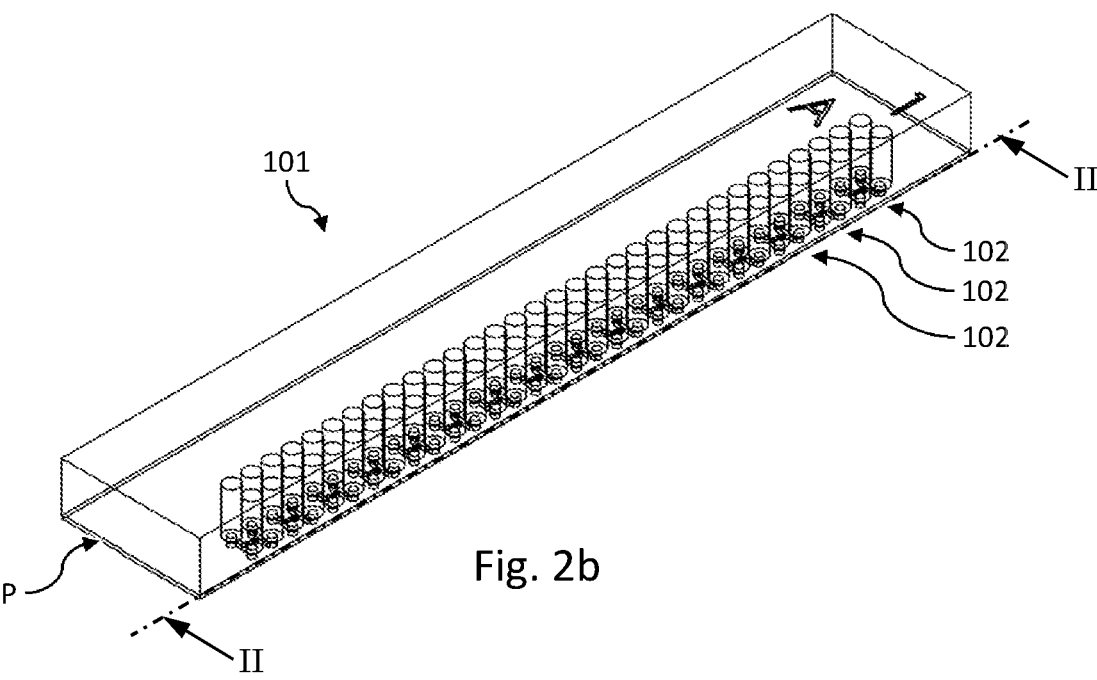
Figure 5A:
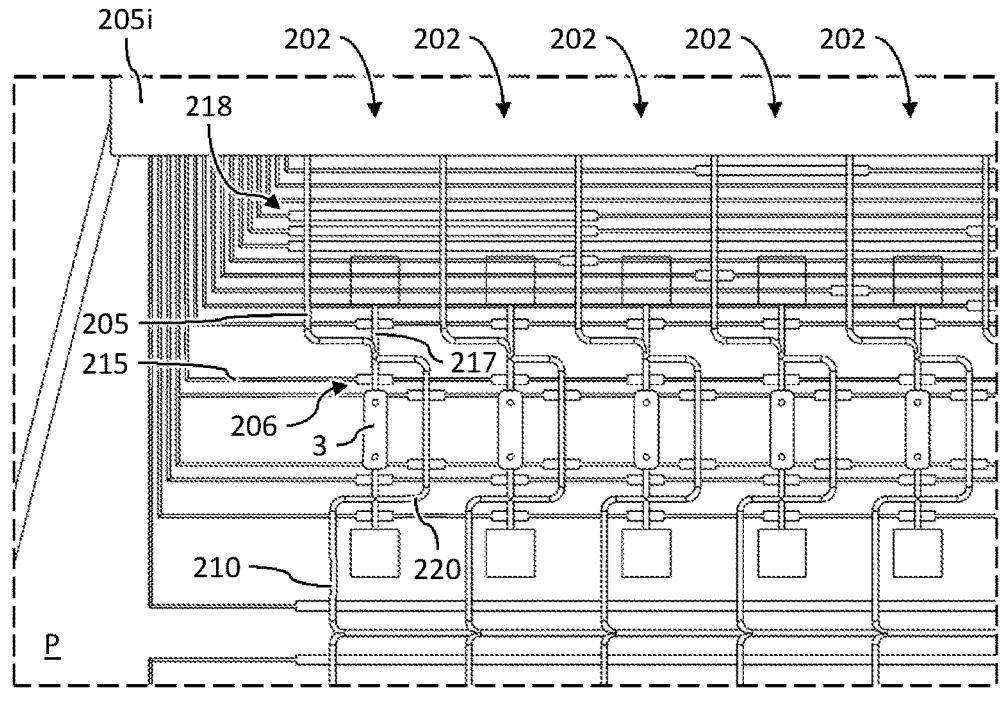
FIG. 5a shows a partial top view of a microfluidic device according to the third embodiment.
Figure 5B:
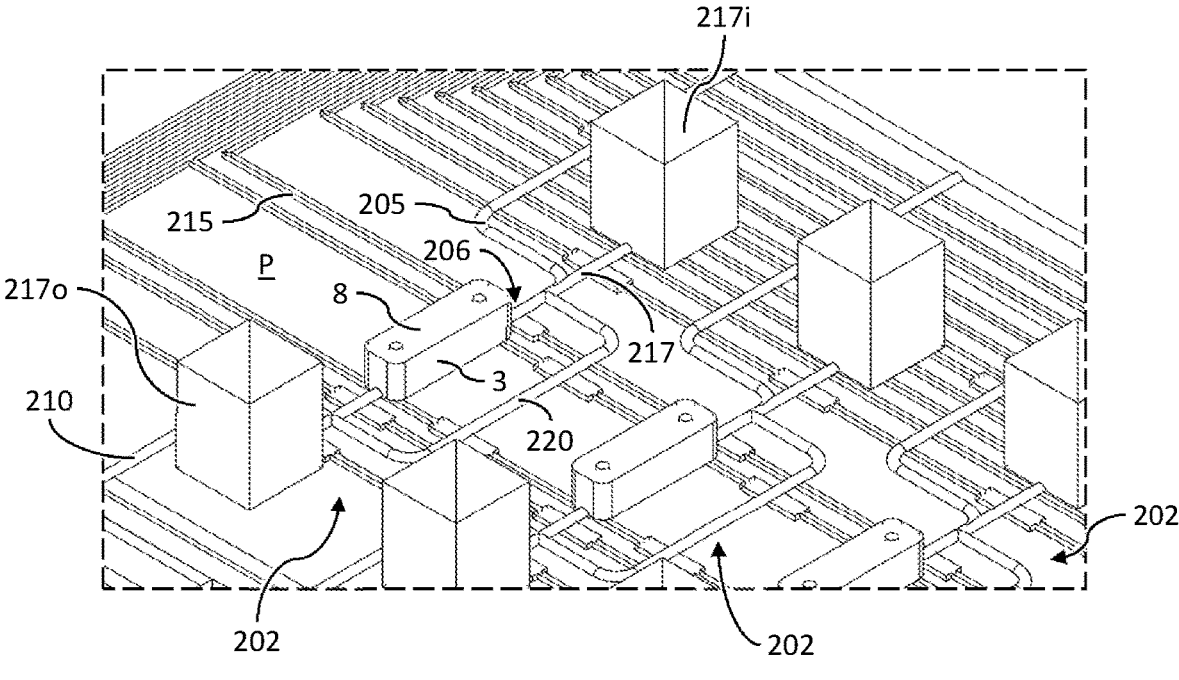
Figure 5C:
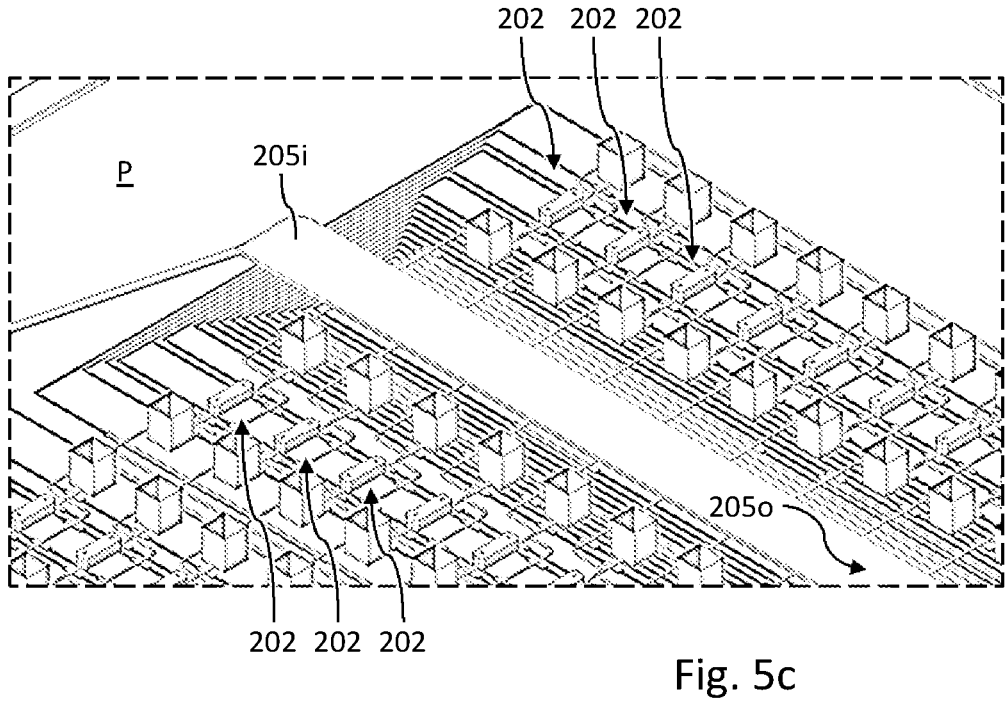
FIG. 5c shows a further partial isometric view of the device of FIGS. 5a and 5b.
Figure 5D:
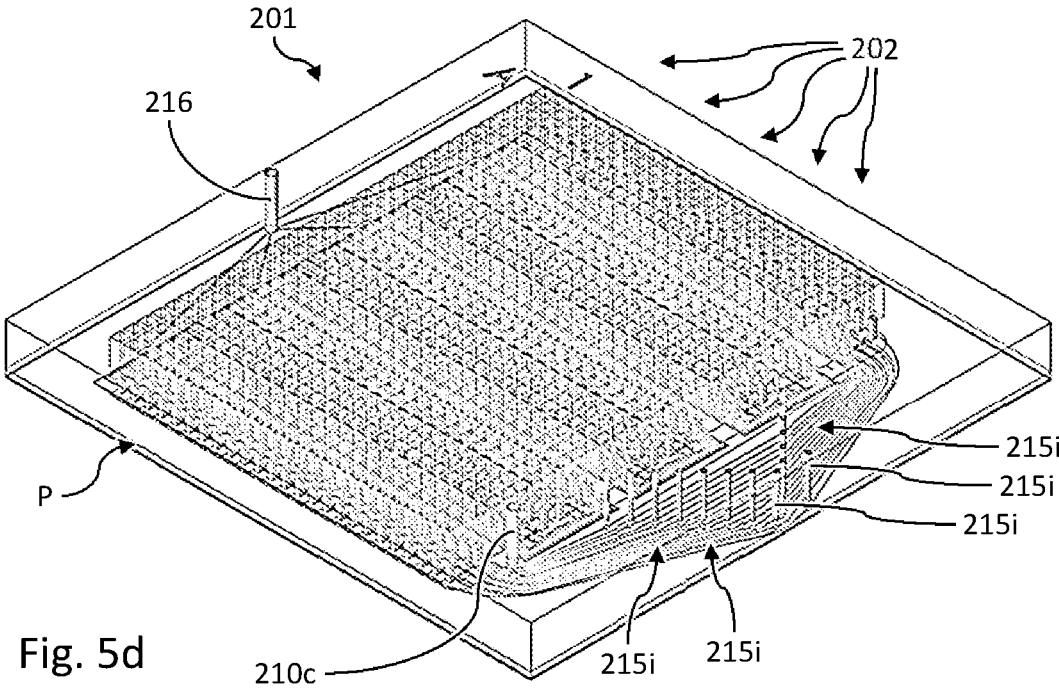
FIG. 5d shows an isometric view of the device of FIGS. 5a-c.

FIGS. 2a and 5d each show a microfluidic device 101, 201 comprising at least one cell culture unit 102, 202 for forming, culturing, growing and/or maintaining a 3D tissue structure S (see FIGS. 7a-c for an example), such as a 3D strip of cardiac tissue.

The at least one cell culture unit 102, 202 comprises (see e.g. FIGS. 1a-b, 3 and 4): a respective culture chamber 3 for culturing cells having a chamber outlet opening 4; and a cell supply channel 105, 205 arranged to guide a microfluidic flow of liquid holding cells between a channel inlet 105i, 205i and a channel outlet 105o, 205o.

As shown, the cell supply channel 105, 205 is provided with a flow inhibitor 106, 206 which is operable to selectively provide a flow inhibiting state or a flow permitting state depending on a fluid pressure at the flow inhibitor 106, 206.

As will be explained further elsewhere in this description, in the first embodiment (see FIGS. 1a-2b) the flow inhibitor 106 comprises a capillary burst valve, whereas in the second and third embodiments (see FIGS. 3-6b) the flow inhibitor 206 comprises a quake valve.

In the flow inhibiting state, the flow inhibitor 106, 206 is configured to substantially inhibit liquid flow between the cell supply channel 105, 205 and the culture chamber 3, wherein, in the flow permitting state, the flow inhibitor 105, 205 is configured to permit such liquid flow such that the cell supply channel 105, 205 is in liquid communication with the culture chamber 3 to supply the culture chamber 3 with cells.

In the examples, the flow inhibitor 106, 206 is arranged adjacent the respective culture chamber 3, in particular at a connection between the cell supply channel 105, 205 and the culture chamber 3.

Figure 1A:
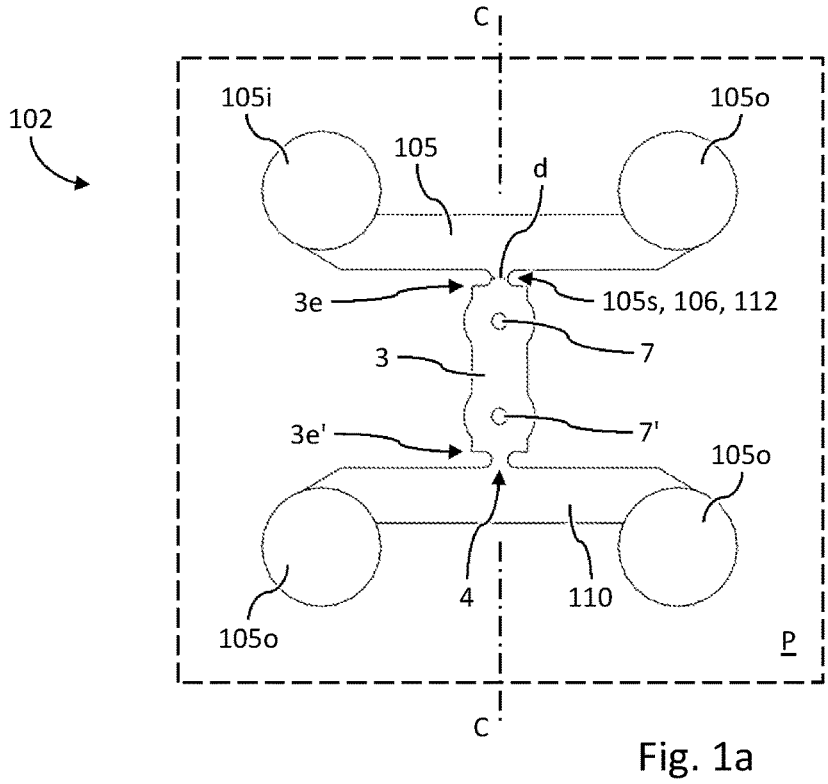
FIG. 1a shows a top view of a cell culture unit of a microfluidic device according to a first embodiment.
Figure 1B:
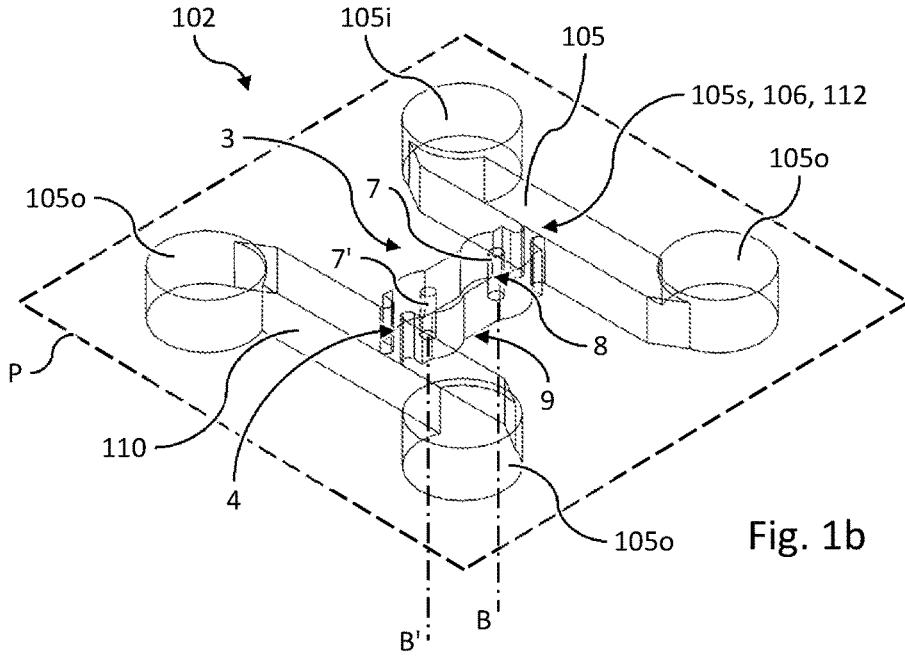

In FIGS. 1a-b one channel inlet 105i and three channel outlets 105o have been indicated with reference signs. Based on the symmetrical design, it will be appreciated that alternatively or additionally any of the elements indicated as outlets 105o can be used as an inlet and that the element indicated as inlet 105i can alternatively or additionally be used as an outlet. Thus, during use, each of the elements 105i, 105o can be used as an inlet and/or as an outlet. Merely for clarity of the drawings only one possible combination of inlet/outlet designations has been indicated therein.

Figure 7A:
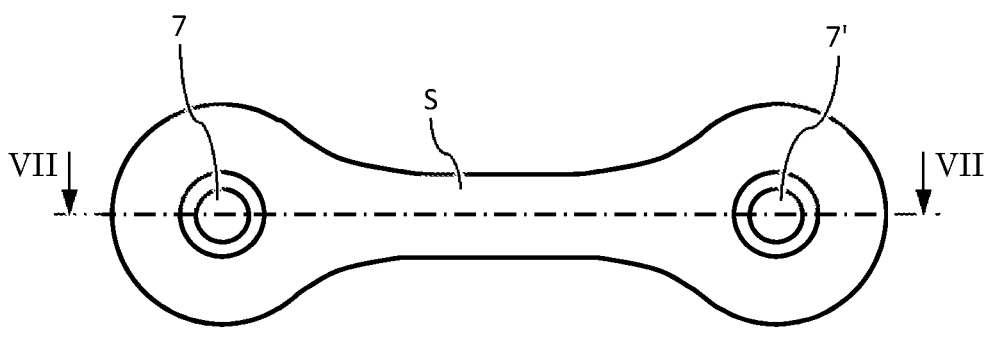
FIG. 7a shows a bottom view of a cultured 3D tissue structure and two associated elastic support structures in an exemplary culture chamber, wherein the tissue structure is in a relaxed state.
Figure 7B:
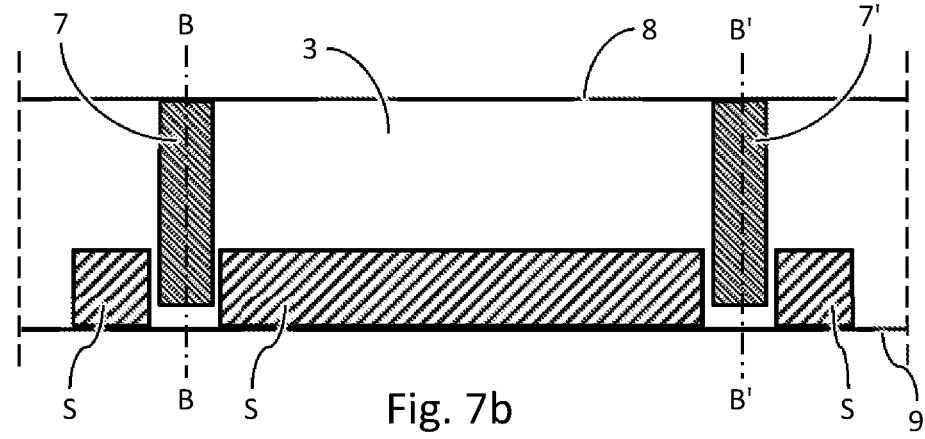
Figure 7C:
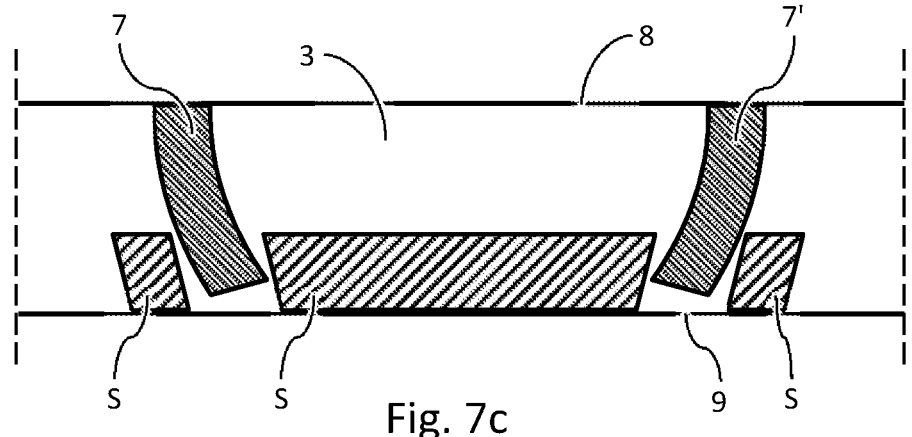
FIG. 7c shows a cross section view similar to FIG. 7b but with the tissue structure in a contracted state.

In the examples shown, with particular reference to FIGS. 7a-c, the culture chamber 3 is provided with at least two mutually spaced apart elastic support structures 7, 7', for example mainly made from silicon and/or plastic, which extend in the culture chamber 3 and which are configured for elastically supporting a tissue formed in the culture chamber 3, in particular a cultured tissue formed from the cells, wherein the elastic support structures 7, 7' are elastically deformable, in particular flexible, in particular to vary a mutual distance of said support structures 7, 7' under influence of a varying contraction force between said support structures 7, 7'.

FIG. 7c shows how such a mutual distance between support structures 7, 7' is thus reduced when the 3D tissue structure S is in a contracted state, in particular reduced compared to the situation shown in FIG. 7b in which the 3D tissue structure S is in a (more) relaxed state.

As shown, at least one, preferably each, of the elastic support structures 7, 7' comprises a respective elastic beam 7, 7', in particular a flexible beam, which is connected to and extends from a wall 8, in particular a top wall 8, of the culture chamber 3. As shown, said beams 7, 7' may be substantially cylindrical.

Preferably a main longitudinal beam axis B, B' (see FIGS. 1b and 7b) of the elastic beam 7, 7', in particular in an unloaded state, extends at an angle to said wall 8, preferably an angle between 45 and 135 degrees, for example an angle of about 90 degrees, wherein preferably said wall 8 extends substantially in parallel to a main device plane P (see e.g. FIG. 1b) in which the microfluidic device 101, 201 extends.

Optionally at least one, preferably at least two, of the elastic support structures 7, 7' comprises an electrode (not explicitly shown) configured for determining an electrophysiological property of the 3D tissue structure S. Alternatively or additionally, an interaction, in particular a mechanical interaction, between the 3D tissue structure S and the support structures 7, 7' may be studied optically e.g. using imaging, in particular video confocal microscopy. One or more mechanical properties, for example a contraction force, of the formed 3D tissue structure S may thus be determined.

The shown elastic support structures 7, 7' are mutually spaced apart by a distance of between 0.1 and 10 mm, preferably between 0.1 and 5 mm, preferably between 0.1 and 3 mm, preferably between 0.1 and 2 mm, preferably between 0.1 and 1 mm, for example about 0.6 mm or about 0.9 mm.

Such a distance may thus be advantageously designed in accordance with one or more other dimensions, e.g. a volume, of the culture chamber, which in turn may be dimensioned based on a predetermined, e.g. minimum, number of cells. Said number of cells may be informed by the type of essay to be performed on the cultured 3D tissue structure.

In the shown embodiments, the bottom wall 9 of the culture chamber 3 is configured to allow imaging of the interior of the culture chamber 3 through said bottom wall 9 using confocal microscopy, in particular in the visible spectrum, wherein at least part of the bottom wall 9 is substantially transparent, wherein preferably a thickness of the bottom wall 9 is in the range of 1 to 1000 μm, preferably in the range of 100 to 500 μm, for example about 150 μm.

As shown, each cell culture unit 102, 202 comprises an outlet channel 110, 210 in fluid communication with the culture chamber 3 separate from the supply channel 105, 205, wherein during use preferably at least one of the outlet channel 110, 210 and the supply channel 105, 205 provides a vent for the culture chamber 3.

In the shown embodiments (see FIGS. 2a-b, 3 and 5a-d), the device 101, 201 comprises the at least one cell culture unit 102, 202 in an array of cell culture units 102, 202, in particular a two-dimensional array (see FIGS. 2a, 5c-d), wherein preferably the array comprises a number of cell culture units 102, 202 in the range of 10 to 2000, more preferably in the range of 50 to 1536, more preferably in the range of 100 to 500, for example about 200 (see FIG. 5d) or about 384 (see FIG. 2a).

In the first embodiment (see FIGS. 1a-2b), the flow inhibitor 106 is formed by a flow path section 105s (see FIGS. 1a-b) of the cell supply channel 105 arranged as a capillary burst valve which is operable by change of a liquid flow pressure of the liquid flowing in the flow path section 105s of the channel 105.

This flow inhibitor 106 is configured to be operated in the flow permitting state by providing liquid with a liquid flow pressure exceeding a threshold flow pressure value, wherein the flow inhibitor 106 is configured to be operated in the flow inhibiting state by providing liquid with a liquid flow pressure below the threshold flow pressure value.

In the shown example, the capillary burst valve 105s provides a substantially bidirectional capillary burst valve 105s, wherein preferably the flow path section 105s is shaped with a central flow constriction 112, the flow path section 105s being substantially symmetrical with respect to a plane of symmetry which is transverse to the flow path section 105s at the central flow constriction 112.

In FIG. 1a, such a plane of symmetry is oriented perpendicular to the plane of the drawing and perpendicular to the main culture chamber axis C.

Measured in a transverse plane to the flow path 105s (for example in the above mentioned plane of symmetry), the flow constriction 112 has a smallest diameter d in the range of 0.01 to 1 mm preferably in the range of 0.01 to 0.5 mm, for example about 0.1 mm.

In the second and third embodiments, see FIGS. 3-6b, the flow inhibitor 206 comprises a quake valve 206 comprising a valve control chamber 213 and a flexible membrane 214 which liquid-tightly separates the cell supply channel 205 from the valve control chamber 213, the valve control chamber 213 being fluidly connected to a valve control channel 215 for supplying control fluid to the control chamber 213 to provide a fluid pressure in the valve control chamber 213.

This flow inhibitor 206 is changeable from the flow inhibiting state to the flow permitting state by reducing the fluid pressure in the valve control chamber 213 with respect to a fluid pressure in the cell supply channel 205, wherein the flow inhibitor 206 is changeable from the flow permitting state to the flow inhibiting state by increasing the fluid pressure in the valve control chamber 213 with respect to the fluid pressure in the cell supply channel 205.

In the flow inhibiting state the flexible membrane 214 is shaped to liquid-tightly seal the supply channel 205 to inhibit liquid flow between the cell supply channel 205 and the culture chamber 3, wherein in the flow permitting state the flexible membrane 214 is shaped to allow liquid flow between the cell supply channel 205 and the culture chamber 3.

The flexible membrane 214 is preferably substantially elastic, i.e. it is biased to return to a respective unloaded or less-loaded state after a respective load is reduced. Specifically, in use, when pressure in the valve control chamber 213 is increased, the flexible membrane 214 may thereby be stretched towards, and preferably onto, a wall of the cell supply channel 205, thereby substantially blocking said channel 205. Upon a subsequent pressure reduction in the valve control chamber 213, the membrane 214 may thus elastically revert to a previous non-blocking position, thereby permitting flow through the channel 205. It will be appreciated that a state and/or position of said membrane 214 may be additionally dependent on a pressure in the cell supply channel 205. Thus, a respective membrane position, and thereby a state of the flow inhibitor 206, may be dependent on a pressure difference between the valve control chamber 213 on the one hand and the cell supply channel 205 on the other hand. In use, for example, the pressure in the valve control chamber 213 may be increased to exceed the pressure in the cell supply channel 205 to bring the flow inhibitor 206 from its flow permitting state to its flow inhibiting state, and vice versa.

As shown for example in FIGS. 3, 5a-b and 6a, the respective cell supply channels 205 of the cell culture units 202 are fluidly connected to each other upstream of the flow inhibitor 206, in particular connected to a common cell supply inlet 216 of the microfluidic device 201.

Figure 3:
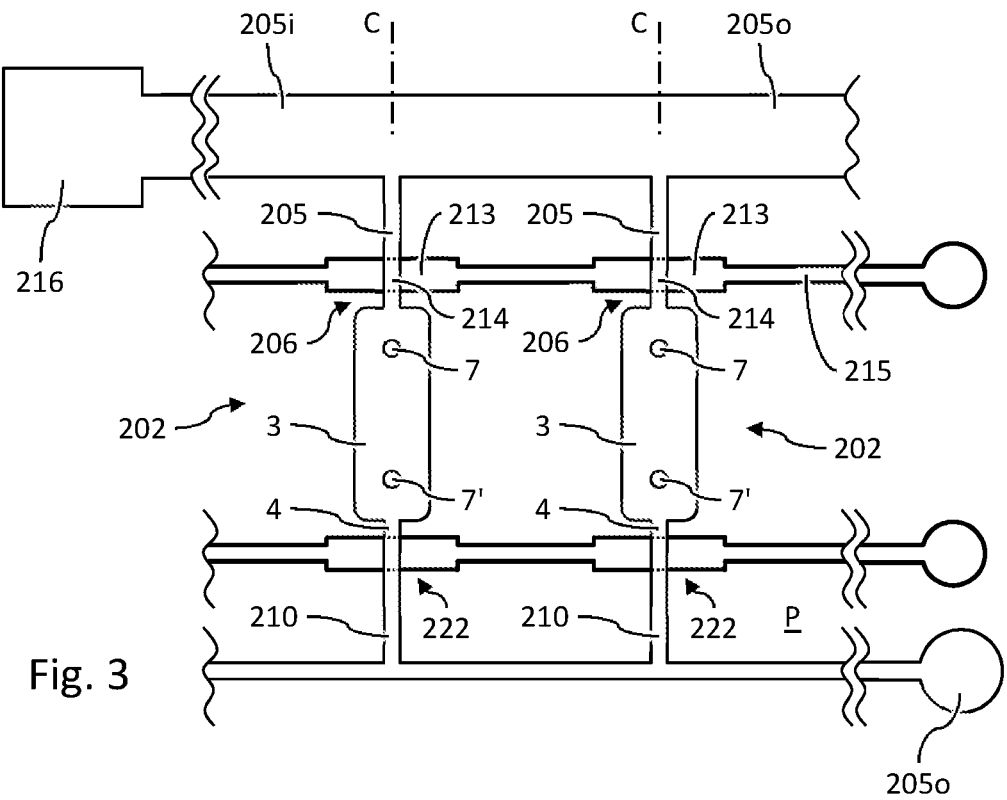
FIG. 3 shows a partial top view of a microfluidic device according to a second embodiment.
Figure 4:
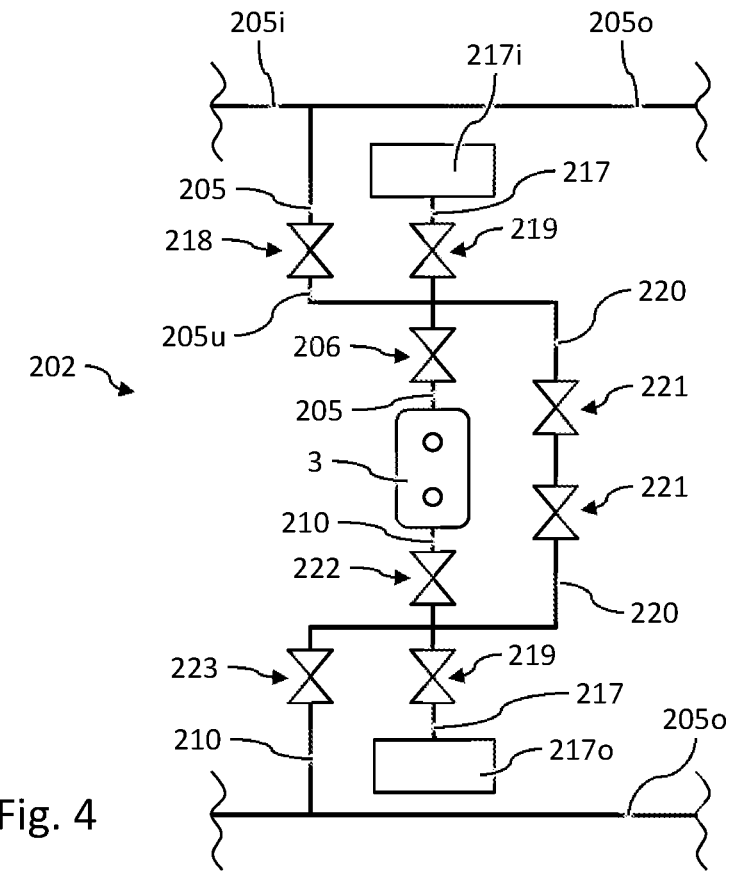
FIG. 4 shows a diagrammatic top view of a cell culture unit of a microfluidic device according to a third embodiment.

FIGS. 3 and 5a-b show that respective valve control chambers 213 of at least two different cell culture units 202 are fluidly connected to the same valve control channel 215 for contemporaneously changing a fluid pressure in each of the respective valve control chambers 213.

In the shown examples of the third embodiment (see FIGS. 4-5b), each cell culture unit 206 comprises a respective agent supply channel 217 arranged to guide a microfluidic flow of liquid holding an agent between an agent inlet 217i and an agent outlet 217o. The agent can be a pharmaceutical compound to be tested, for example.

As shown, for each cell culture unit 202 the device 201 is configured to permit a flow of liquid from the respective agent supply channel 217 to the respective culture chamber 3 of the cell culture unit 202 while at the same time inhibiting a flow of liquid from said agent supply channel 217 to one or more, preferably all, culture chambers 3 of the other cell culture units 206 of the device 201.

In the shown examples, the agent supply channel 217 fluidly connects to a path section 205u of the cell supply channel 205 which section is upstream of the flow inhibitor 206, wherein the cell supply channel 205 is provided with a further flow inhibitor 218, in particular a quake valve, which is arranged upstream of said section 205u of the cell supply channel 205 and configured to inhibit, at least selectively inhibit, a flow of liquid from said section 205u to a cell supply channel 205 of another one of the cell culture units 202.

In the respective examples, the agent supply channel 217 is provided with a respective flow inhibitor 219, in particular a quake valve, for selectively inhibiting a liquid flow through the agent supply channel 217.

In the third embodiment, the cell supply channel 205 is provided with a bypass channel 220 arranged to guide a flow of liquid between the channel inlet 205i and the channel outlet 205o and/or a flow of liquid between the agent inlet 217i and the agent outlet 217o without entering the respective culture chamber 3, wherein preferably the bypass channel 220 is provided with one or more respective flow inhibitors 221, in particular one or more quake valves, for selectively inhibiting a liquid flow through the bypass channel 220.

Figure 6A:
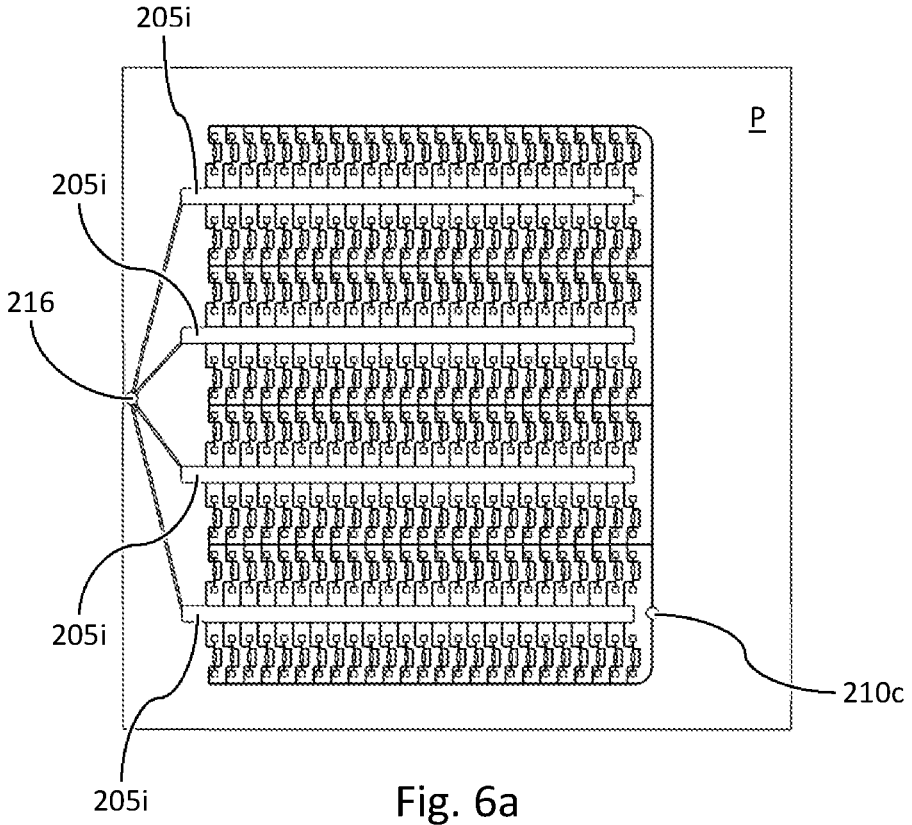
FIG. 6a shows a top view of a first horizontal level of the device of FIGS. 5a-d.
Figure 6B:
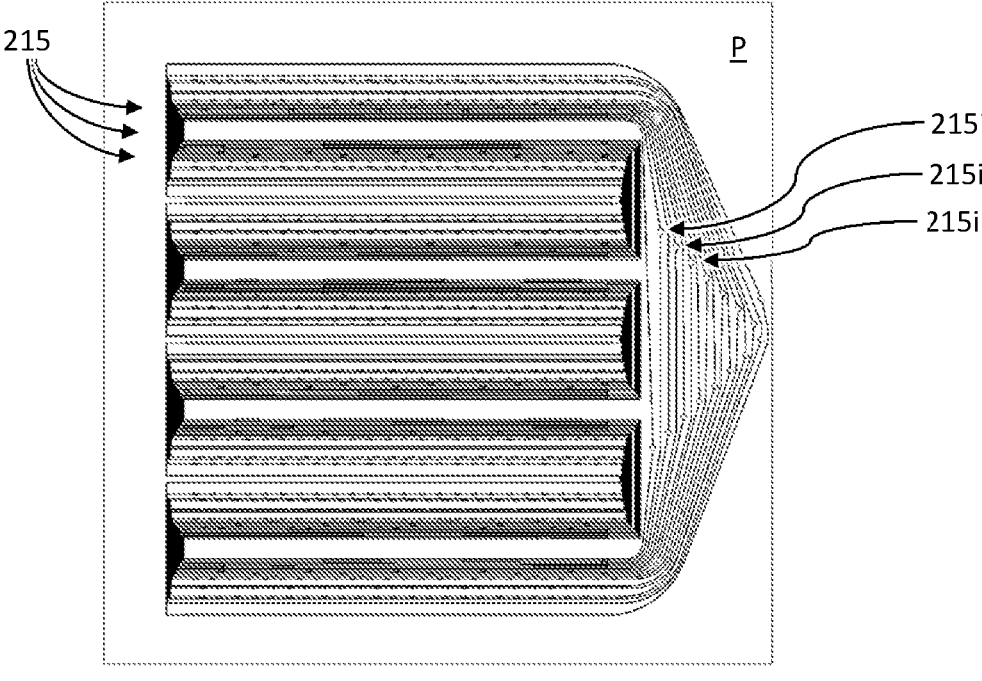
FIG. 6b shows a top view of a second horizontal level of the device of FIGS. 5a-d.

FIG. 6a shows a top view of a first horizontal level of the device 201 according to the third embodiment; FIG. 6b shows a top view of a respective second horizontal level of the device 201. In the device, the second horizontal level may be positioned immediately below the first horizontal level. As shown, the second horizontal level (FIG. 6b) comprises a set of closed-loop valve control channels 215 which run along the array of cell culture units 202 which are otherwise mainly arranged in the first level (FIG. 6a). The valve control channels 215 run substantially mutually in parallel along a substantially winding trajectory. Each valve control channel 215 is provided with one or more respective valve control channel interfaces 215i for connecting an external pressure controller, e.g. comprising a pump, to the respective channel. Each valve control channel 215 comprises a plurality of valve control chambers, wherein in particular each channel 215 has respective chambers in mutually different positions to enable a large number of different combinations of valve control chambers being pressurized simultaneously. In this way a particular compact yet versatile configuration is obtained.

In particular, such a configuration can enable that fluid flow from the common inlet 216 to the individual culture chambers 3 can be controlled individually for each cell culture unit 202 so that said culture chambers can be filled with fluid (e.g. containing cells) one by one, for example. Substantially equal distribution of cells among the culture chambers 3 can thus be provided reliably, in particular without elaborate pipetting efforts.

With reference to the drawings and to the above described exemplary embodiments of the microfluidic device, an exemplary method of forming, culturing, growing and/or maintaining at least one 3D tissue structure S, such as a 3D strip of cardiac tissue, comprises: providing a microfluidic device 101, 201 according to any of the preceding claims; supplying cells for the tissue structure into the respective culture chamber 3 of the at least one cell culture unit 102, 202 via the cell supply channel 105, 205, wherein the respective flow inhibitor 106, 206 is operated in the flow permitting state; and subsequently operating the respective flow inhibitor 106, 206 in the flow inhibiting state, thereby inhibiting the cells from exiting the culture chamber 3 via the flow inhibitor 106, 206.

Subsequently operating the flow inhibitor 106, 206 in the flow inhibiting state may comprise controlling a fluid pressure at the flow inhibitor 106, 206, for example a fluid pressure in a respective valve control chamber 213.

When the microfluidic device 201 comprises the at least one cell culture unit 202 in an array of cell culture units 202 and the respective cell supply channels 205 of the cell culture units 202 are fluidly connected to a common cell supply inlet 216, supplying cells into the respective culture chamber 3 of the at least one cell culture unit 202 preferably comprises supplying cells for a plurality of cell culture units 202 into the common cell supply inlet 216 and subsequently allowing the cells to travel from said cell supply inlet 216 through the respective cell supply channels 205 to the respective culture chambers 3, for example subsequently to neighboring culture chambers 3.

The method may comprise supplying an agent, for example a pharmaceutical compound, into the culture chamber 3, for example subsequently via a respective agent inlet 217i and a respective agent supply channel 217 of the respective cell culture unit 202.

The method may comprise supplying a gellable substance into the respective culture chamber 3, preferably together with supplying the cells, wherein for example the gellable substance and the cells are together supplied in a microfluidic flow of liquid through the cell supply channel 105, 205; and subsequently allowing the gellable substance to form a gel in the culture chamber 3, thereby suspending cells in the culture chamber 3 in the formed gel.

The gellable substance may form a biodegradable gel in the culture chamber 3. In that case the method preferably comprises allowing the cells in the culture chamber 3 to at least partly degrade the biodegradable gel, preferably such that the cells migrate towards each other during the at least partial degrading to form a clump of cells in the culture chamber 3, in particular a clump of cells together forming a 3D tissue structure S which connects to one or more elastic support structures 7, 7' in the culture chamber 3.

An exemplary method of performing an assay on at least one 3D tissue structure S comprises: forming at least one 3D tissue structure S, for example a strip of cardiac tissue, in particular using a microfluidic device 101, 201; and measuring an activity of the at least one 3D tissue structure (S), in particular a tissue movement and/or an electrical activity.

In this way, one or more muscle contraction properties of the 3D tissue structure may be determined, for example one or more of: an absolute force of contraction, a speed of contraction, a speed of relaxation, a contraction duration and a contraction interval. Such a muscle contraction property can subsequently be compared among different tissue structures and/or within one structure over time in order to assess effects, at least relative effects, of an assay variable, for example a variable associated with a pharmaceutical compound supplied to the 3D tissue structure.

An exemplary system for performing an assay on at least one 3D tissue structure S comprises: a microfluidic device 101, 201; and a measurement device (not shown), for example comprising a video camera, for measuring a property and/or an activity of the at least one 3D tissue structure S.

The system may further comprise a source of cells, e.g. a pipetting device holding cells, for supplying cells to the at least one culture chamber 3 via an inlet 216 of the device 101, 201.

The system may further comprise a pump (not shown), e.g. external of and connectable to the microfluidic device 101, 201, for changing a fluid pressure in the device 101, 201.

The microfluidic device 101, 201 can thus be used for forming, culturing, growing and/or maintaining, and studying, at least one 3D tissue structure S, preferably an array of separate 3D tissue structures in respective culture chambers 3. The number of separate 3D tissue structures in the array can thus be in the range of 10 to 1000, more preferably in the range of 50 to 1536, more preferably in the range of 100 to 500, for example about 200 or about 384.

While the invention has been explained using exemplary embodiments and drawings, it will be appreciated that these are not to be construed as limiting the scope of the invention in any way, which scope is provided by the claims. Many variations, alternatives and extensions are possible, as will be clear to the skilled person. For example, a flow inhibitor may be designed without a capillary burst valve and/or without a quake valve, for example with a different type of microfluidic valve. A culture chamber may be provided or associated with any positive number of flow inhibitors. Microfluidic spaces such as culture chambers, channels, inlets, outlets and fluidic connections may be shaped and dimensioned in various ways. A design of the flow inhibitor is not necessarily linked to any number of cell culture units per device. A cell tissue structure may comprise heart cells and/or one or more different types of cells. Cells and/or tissue structures may be cultured for different purposes than performing assays. Cells cultured in distinct culture chambers may or may not be connected or connectable.

Example of Use

Beating cardiomyocytes are prepared as follows. Human embryonic stem cells (hESC) and/or human induced pluripotent stem cells (hiPSC) coming from in vitro cell cultures or from commercial available sources are cultured on Vitronectin Recombinant Human Protein (Life technologies) coated plastic plates in E8 medium (Life Technologies). The hESC and hiPSC are passaged using PBS (Life Technologies) containing EDTA 0.5 mM (Life Technologies) or TryplE (Gibco).

Differentiation into the cardiac lineage is induced in a monolayer as described e.g. in Elliott et al., 2011; van den Berg, Elliott, Braam, Mummery, & Davis, 2016. Briefly, $25 \times 10^3/cm^2$ are seeded on plates coated with 75 µg/mL (growth factor reduced) Matrigel (Corning) the day before differentiation (day −1). At day 0, cardiac mesoderm is induced by changing E8 to BPEL medium (Bovine Serum Albumin [BSA] Polyvinyl alcohol Essential Lipids; (Ng et al., 2008)), supplemented with a mixture of cytokines (20 ng/mL BMP4, R&D Systems; 20 ng/mL ACTIVIN A, Miltenyi Biotec; 1.5 µM GSK3 inhibitor CHIR99021, Axon Medchem). After 3 days, cytokines are removed and a Wnt inhibitor (5 µM, XAV939, Tocris Bioscience) is added for 3 days. BPEL medium is refreshed every 3-4 days.

To generate 3D cardiac tissue the beating cardiomyocytes are dissociated using TryplE 1× for 10 minutes, collected, spun down and resuspended in cell culture medium.

The resuspended cells are mixed at a final density of $5 \times 10^6$ to $20 \times 10^6$ cells/mL with 2 to 5 mg/mL bovine fibrinogen (stock solution: 200 mg/mL fibrinogen in NaCl 0.9%, Sigma F8630), 100 µl/mL Matrigel (BD Bioscience 356235). To the final mix thrombin is added at 1:300 (100 U/mL, Sigma Aldrich T7513), resuspended well and the entire solution is pipetted into the fluidic channel.

Once the thrombine is added, the fibrinogen will gelate within 10 minutes. This time can be modified to be longer or shorter depending on multiple factors (thrombine concentration, temperature, presence of thrombine inhibitors, among other factors). For Collagen the gelation is driven by temperature and pH. As will be explained further, the cell/fibrinogen mixture is driven into the culture chambers 3 via the microfluidic routing 105, 205 and enters the chambers 3.

In case of use of the above-described first embodiment (see FIGS. 1a-2b), for each cell culture unit 102 the cell/fibrinogen mixture is pipetted into the respective inlet 105i that is connected to the cell supply channel 105 that is connect to the culture chamber 3. The liquid goes into the channel 105 and then into the chamber 3. The liquid gets pinned in the chamber 3 due to the capillary burst valves 105s and the remaining liquid in the channel 105 is removed, wherein the channel 105 is emptied (liquid is replaced with air). This process is repeated for all culture units 102 using an automated pipetter. After the fibrinogen crosslinks, the cell supply channels 105 are filled with medium.

Alternatively, in case of use of the above-described third embodiment (FIGS. 4-6b), the cell/fibrinogen mixture is pipetted into the main inlet 216. The main inlet 216 is then connected to a pressure driving pump (which is external to the microfluidic device 201). This pressure pushes the liquid through the fluidic routing 216, 205i, 205. By actuating the quake valves 206 the cell mixture is directed to each chamber 3 one by one. After all chambers 3 are filled, the valves 206, 222 at the inlet and outlet of the chambers 3 are closed and the fluidic routing 216, 205i, 205 is then immediately washed with medium or PBS. After the fibrinogen crosslinks, the fluidic channels 205 are filled with medium. The microfluidic device 101, 201 is put in a 37° Celsius, 5% CO2 humidified cell culture incubator for further culture and tissue formation.

After the fibrinogen has gelated (becoming a fibrin network), the cells become encapsulated and therefore stuck in a 3D arrangement. The fibrin network is porous and degradable, so the medium can be perfused through and the cells start secreting metalloproteinases (MT1-MMP) and plasmin that degrade the fibrin network. Since the cells are slowly degrading the fibrin network around them, they start migrating towards each other in the 3D space. With this degradation the fibrin is separated from the walls of the chamber 3 and the cells start migrating toward the center of the tissue. Due to this, the tissue shape will be determined by the initial shape of the chamber 3. In this case the shape of the chamber 3 is elongated and therefore the final shape of the tissue is a strip (cylindrical because the width and height of the chamber are equal). Since the pillars 7, 7' are present inside the 3D space of the chamber 3, the tissue has to form around these pillars 7, 7', and consequently the tissue will be anchored to such pillars 7, 7'.

After the cells compact together into a tissue, the muscle cells start applying force into the anchoring points on the pillars 7, 7'. The muscle cells align their sarcomeres in the direction of the anchoring points in order to increase the force output applied on those anchor points (pillars). Since the pillars 7, 7' are hanging from the ceiling 8, this force makes the pillars 7, 7' bend. Using a high-speed camera this bending movement of the pillars is captured and processed into a force using the young's modulus of the pillars 7, 7'. Since the main function of the heart and muscles is to contract, measuring contraction force gives the most relevant information about the health condition of the heart and muscles. With this assay absolute force of contraction, speed of contraction, speed of relaxation, contraction duration and contraction interval, which is a measurement of arrhythmias, may be measured.

LIST OF REFERENCE SIGNS

101, 201 Microfluidic device
102, 202 Cell culture unit
3 Culture chamber
3e, 3e' Axial end of culture chamber
4 Chamber outlet opening
105, 205 Cell supply channel
105i, 205i Channel inlet of cell supply channel
105o, 205o Channel outlet of cell supply channel
105s Flow path section of cell supply channel arranged as capillary burst valve
205u Path section of the cell supply channel upstream of the flow inhibitor
106, 206 Flow inhibitor of cell supply channel
7, 7' Elastic beam
8. Top wall of culture chamber
9. Bottom wall of culture chamber
110, 210 Outlet channel
210c Common outlet
112 Central flow constriction
213 Valve control chamber
214 Flexible membrane
215 Valve control channel
215i Valve control channel interface
216 Common cell supply inlet
217 Agent supply channel
217i Agent inlet
217o Agent outlet
218 Further flow inhibitor of cell supply channel
219 Flow inhibitor of agent supply channel
220 Bypass channel

221 Flow inhibitor of bypass channel
222 Flow inhibitor of outlet channel
223 Further flow inhibitor of outlet channel
B, B' Main longitudinal beam axis
C. Main longitudinal chamber axis
d. Smallest diameter of flow constriction
P. Main device plane
S. 3D tissue structure

The invention claimed is:

1. A microfluidic device comprising at least one cell culture unit for forming, culturing, growing and/or maintaining a 3D tissue structure of cardiac tissue, wherein the at least one cell culture unit comprises:
   a respective culture chamber for culturing cells having a chamber outlet opening; and
   a cell supply channel arranged to guide a microfluidic flow of liquid holding cells between a channel inlet and a channel outlet,
   wherein the cell supply channel is provided with a flow inhibitor which is operable to selectively provide a flow inhibiting state or a flow permitting state depending on a fluid pressure at the flow inhibitor,
   wherein, in the flow inhibiting state, the flow inhibitor is configured to inhibit liquid flow between the cell supply channel and the culture chamber, wherein, in the flow permitting state, the flow inhibitor is configured to permit such liquid flow such that the cell supply channel is in liquid communication with the culture chamber to supply the culture chamber with cells,
   wherein the culture chamber is provided with at least two mutually spaced apart elastic support structures which extend in the culture chamber and which are configured for elastically supporting a tissue formed from the cells formed in the culture chamber, wherein the elastic support structures are elastically deformable or flexible to vary a mutual distance of said support structures under influence of a varying contraction force between said support structures.

2. The microfluidic device according to claim 1, wherein the flow inhibitor is arranged adjacent the respective culture chamber at a connection between the cell supply channel and the culture chamber.

3. The microfluidic device according to claim 1, wherein at least one of the elastic support structures comprises an elastic beam which is connected to and extends from a wall of the culture chamber,
   wherein a main longitudinal beam axis of the elastic beam in an unloaded state extends at an angle to said wall between 45 and 135 degrees,
   wherein said wall extends parallel to a main device plane in which the microfluidic device extends.

4. The microfluidic device according to claim 1, wherein one or more of the elastic support structures is configured to enable, during use, determination of one or more contraction properties of an associated 3D tissue structure.

5. The microfluidic device according to claim 1, wherein at least one of the elastic support structures comprises an electrode configured for determining an electrophysiological property of the 3D tissue structure.

6. The microfluidic device according to claim 1, wherein the elastic support structures are mutually spaced apart by a distance of between 0.1 and 10 mm.

7. The microfluidic device according to claim 1, wherein a bottom wall of the culture chamber is configured to allow imaging of an interior of the culture chamber through said bottom wall using confocal microscopy, wherein at least part of the bottom wall is transparent, wherein a thickness of the bottom wall is in the range of 1 to 1000 µm.

8. The microfluidic device according to claim 1, wherein the at least one cell culture unit comprises an outlet channel in fluid communication with the culture chamber separate from the cell supply channel, wherein during use at least one of the outlet channel and the supply channel provides a vent for the culture chamber.

9. The microfluidic device according to claim 1, comprising the at least one cell culture unit in an array of cell culture units.

10. The microfluidic device according to claim 9, wherein the array comprises a number of cell culture units in the range of 10 to 2000.

11. The microfluidic device according to claim 10, wherein the cell supply channel of the at least one cell culture unit is fluidly connected to other cell supply channels upstream of the flow inhibitor and connected to a common cell supply inlet.

12. The microfluidic device according to claim 11, wherein each cell culture unit comprises a respective agent supply channel arranged to guide a microfluidic flow of liquid holding an agent, between an agent inlet and an agent outlet, wherein for each cell culture unit the device is configured to permit a flow of liquid from the respective agent supply channel to the culture chamber of the at least one cell culture unit while at the same time inhibiting a flow of liquid from said agent supply channel to one or more culture chambers of other cell culture units of the device.

13. The microfluidic device according to claim 12, wherein the agent supply channel fluidly connects to a path section of the cell supply channel which section is upstream of the flow inhibitor, wherein the cell supply channel is provided with a further flow inhibitor which is arranged upstream of said section of the cell supply channel and configured to at least selectively inhibit a flow of liquid from said section to a cell supply channel of another one of the cell culture units.

14. The microfluidic device according to claim 12, wherein the agent supply channel is provided with a respective flow inhibitor for selectively inhibiting a liquid flow through the agent supply channel.

15. The microfluidic device according to claim 10, wherein valve control chambers of at least two different cell culture units are fluidly connected to a same valve control channel for contemporaneously changing a fluid pressure in each of the valve control chambers.

16. The microfluidic device according to claim 1, wherein the flow inhibitor is formed by a flow path section of the cell supply channel arranged as a capillary burst valve which is operable by change of a liquid flow pressure of the liquid flowing in a flow path section of the cell supply channel, wherein the flow inhibitor is configured to be operated in the flow permitting state by providing liquid with a liquid flow pressure exceeding a threshold flow pressure value, wherein the flow inhibitor is configured to be operated in the flow inhibiting state by providing liquid with a liquid flow pressure below the threshold flow pressure value.

17. The microfluidic device according to claim 16, wherein the capillary burst valve provides a bidirectional capillary burst valve, wherein the flow path section is shaped with a central flow constriction, the flow path section being symmetrical with respect to a plane of symmetry which is transverse to the flow path section at the central flow constriction.

18. The microfluidic device according to claim 12, wherein, measured in a transverse plane to the flow path, the central flow constriction has a smallest diameter (d) in the range of 0.01 to 1 mm.

19. The microfluidic device according to claim 1, wherein the flow inhibitor comprises a quake valve comprising a valve control chamber and a flexible membrane which liquid-tightly separates the cell supply channel from the valve control chamber, the valve control chamber being fluidly connected to a valve control channel for supplying control fluid to the valve control chamber to provide a fluid pressure in the valve control chamber, wherein the flow inhibitor is changeable from the flow inhibiting state to the flow permitting state by reducing the fluid pressure in the valve control chamber with respect to a fluid pressure in the cell supply channel, wherein the flow inhibitor is changeable from the flow permitting state to the flow inhibiting state by increasing the fluid pressure in the valve control chamber with respect to the fluid pressure in the cell supply channel, wherein, in the flow inhibiting state, the flexible membrane is shaped to liquid-tightly seal the supply channel to inhibit liquid flow between the cell supply channel and the culture chamber, wherein, in the flow permitting state, the flexible membrane is shaped to allow liquid flow between the cell supply channel and the culture chamber.

20. The microfluidic device according to claim 19, wherein the cell supply channel is provided with a bypass channel arranged to guide a flow of liquid between the channel inlet and the channel outlet and/or a flow of liquid between an agent inlet and an agent outlet without entering the respective culture chamber, wherein the bypass channel is provided with one or more respective flow inhibitors for selectively inhibiting a liquid flow through the bypass channel.

21. A method of forming, culturing, growing and/or maintaining at least one 3D tissue structure, the method comprising:

providing a microfluidic device according to claim 1;

supplying cells for the at least one 3D tissue structure into the respective culture chamber of the at least one cell culture unit via the cell supply channel, wherein the flow inhibitor is operated in the flow permitting state; and subsequently operating the flow inhibitor in the flow inhibiting state, thereby inhibiting the cells from exiting the culture chamber via the flow inhibitor.

22. The method according to claim 21, wherein subsequently operating the flow inhibitor in the flow inhibiting state comprises controlling the fluid pressure at the flow inhibitor.

23. The method according to claim 21, wherein the microfluidic device comprises the at least one cell culture unit in an array of cell culture units, wherein the the cell supply channel of the at least one cell culture unit is fluidly connected to a common cell supply inlet, wherein supplying cells into the respective culture chamber of the at least one cell culture unit comprises supplying cells for a plurality of cell culture units into the common cell supply inlet and subsequently allowing the cells to travel from said cell supply inlet through each cell supply channel to the respective culture chambers.

24. The method according to claim 21, further comprising:

supplying an agent into the culture chamber via a respective agent inlet and a respective agent supply channel of the respective cell culture unit.

25. The method according to claim 21, further comprising:

supplying a gellable substance into the respective culture chamber, wherein the gellable substance and the cells are together supplied in a microfluidic flow of liquid through the cell supply channel; and subsequently allowing the gellable substance to form a gel in the culture chamber, thereby suspending cells in the culture chamber in the formed gel.

26. The method according to claim 25, wherein the gellable substance forms a biodegradable gel in the culture chamber, wherein the method further comprises allowing the cells in the culture chamber to at least partly degrade the biodegradable gel such that the cells migrate towards each other during the at least partial degrading to form a clump of cells in the culture chamber said clump of cells together forming a 3D tissue structure which connects to one or more elastic support structures in the culture chamber.

27. A method of performing an assay on at least one 3D tissue structure, comprising:

forming at least one 3D tissue structure according to the method of claim 21; and measuring tissue movement and/or an electrical activity of the at least one 3D tissue structure.

28. A system for performing an assay on at least one 3D tissue structure, comprising:

a microfluidic device according to claim 1; and a measurement device and/or a video camera, for measuring a property and/or an activity of the at least one 3D tissue structure.

29. The system according to claim 28, further comprising: a source of cells for supplying cells to the culture chamber via an inlet of the device;

and/or a pump for changing a fluid pressure in the device.

* * * * *